United States Patent [19]

Fogarty

[11] Patent Number: 5,141,677
[45] Date of Patent: Aug. 25, 1992

[54] METHOD OF HOT STAMPING INTRAOCULAR LENS BODIES

[75] Inventor: Terry M. Fogarty, Hudson, Wis.
[73] Assignee: Minnesota Mining and Manufacturing Company, St. Paul, Minn.
[21] Appl. No.: 643,415
[22] Filed: Jan. 22, 1991
[51] Int. Cl.$^5$ ............................................. B29D 11/00
[52] U.S. Cl. .................................... 264/1.4; 264/1.7; 264/2.3; 264/2.4; 264/2.7; 264/23
[58] Field of Search ..................... 264/1.7, 2.2, 2.4, 2.6, 264/2.7, 1.4, 23, 2.3

[56] References Cited

U.S. PATENT DOCUMENTS

| | | | |
|---|---|---|---|
| 2,292,917 | 8/1942 | Williams | 264/2.2 |
| 2,302,918 | 11/1942 | Smith | 264/2.7 |
| 2,332,674 | 10/1943 | Smith | 264/2.4 |
| 2,443,390 | 6/1948 | Kingston | 264/1.7 |
| 4,153,457 | 5/1979 | Kellie | 96/27 H |
| 4,210,391 | 7/1980 | Cohen | 351/161 |
| 4,242,761 | 1/1981 | Chase et al. | 3/13 |
| 4,315,337 | 2/1982 | Choyce | 3/13 |
| 4,338,005 | 7/1982 | Cohen | 351/161 |
| 4,340,283 | 7/1982 | Cohen | 351/161 |
| 4,384,097 | 5/1983 | Wingler et al. | 526/328.5 |
| 4,533,397 | 8/1985 | Wingler | 106/181 |
| 4,575,372 | 3/1986 | Gundersen | 623/6 |
| 4,636,211 | 1/1987 | Nielsen et al. | 623/6 |
| 4,668,446 | 5/1987 | Kaplan et al. | 264/1.7 |
| 4,704,016 | 11/1987 | de Carle | 351/161 |
| 4,737,322 | 4/1988 | Bruns et al. | 264/1.7 |
| 4,753,653 | 6/1988 | Bissonette et al. | 623/6 |
| 4,769,033 | 9/1888 | Nordan | 623/6 |
| 4,793,953 | 12/1988 | Maus | 264/2.5 |
| 4,813,955 | 3/1989 | Archatz et al. | 623/6 |
| 4,869,588 | 9/1989 | Frieder et al. | 351/168 |
| 4,917,681 | 4/1990 | Nordan | 623/6 |
| 4,936,849 | 6/1990 | Knoll et al. | 623/6 |
| 4,950,057 | 8/1990 | Shirayanagi | 351/169 |
| 4,952,048 | 8/1990 | Frieder et al. | 351/177 |

FOREIGN PATENT DOCUMENTS

| | | |
|---|---|---|
| 0131227A2 | 1/1985 | European Pat. Off. |
| 0170141A3 | 5/1986 | European Pat. Off. |
| 59-124819 | 7/1984 | Japan . |
| 59-124820 | 7/1984 | Japan . |
| 61-95912 | 5/1986 | Japan . |

OTHER PUBLICATIONS

'Perspex'—*Cast Acrylic Sheet Properties and Fabrication Techniques*—Imperial Chemical Industries 'Perspex' Technical Service Note PX 127, pp. 1-21.
*Ultra Violet Absorbing Grades of 'Perspex' Acrylic Sheet*—Imperial Chemical Industries 'Perspex' Technical Data Sheet PX TD 219, pp. 1-3.
*'Perspex' CQ Cast Acrylic Sheet for Clinical Applications*—Imperial Chemical Industries 'Perspex' Technical Data Sheet PX tD 232, pp. 1-2.
*Current Concepts of Multifocal Intraocular Lenses*, Edited by Maxwell et al.; Title page cover, pp. 1-3, and pp. 8-11, 1991.
*Refractive Surgery*—Journal of Cataract Refractive Surgery, pp. 415-427, Jul. 1990.

Primary Examiner—James Lowe
Attorney, Agent, or Firm—Gary L. Griswold; Walter N. Kirn; Walter C. Linder

[57] ABSTRACT

A method for manufacturing an intraocular lens from a cell cast sheet of high molecular weight polymethylmethracrylate (PMMA). A lens blank having a lens generation area with a surface contoured to correspond to the desired contour of the finished lens is machined from the sheet of PMMA to a predetermined precompensated size larger than desired to acccommodate normalizing shrinkage. The lens blank is normalized by heating the blank in a vacuum oven. The vacuum is released from the oven by introducing dry nitrogen. A stamping die is provided. An optical embossing surface of the stamping die is contoured as a physical negative of the lens generation area and bears a physical negative of the desired optical surface structure of the lens, such as a multifocal diffractive zone plate. The embossing surface of the stamping die is forced into engagement with the surface of the lens blank at a predetermined stamping pressure and for a predetermined stamping dwell time. Sufficient heat or ultrasonic energy is applied to the lens generation area of the lens blank to heat the lens generation area to a temperature between the glass transition temperature and the melt temperature of the polymer, and emboss the surface structure onto the lens generation area. The embossing surface of the stamping die is removed from the lens blank following the expiration of the stamping dwell time.

47 Claims, 11 Drawing Sheets

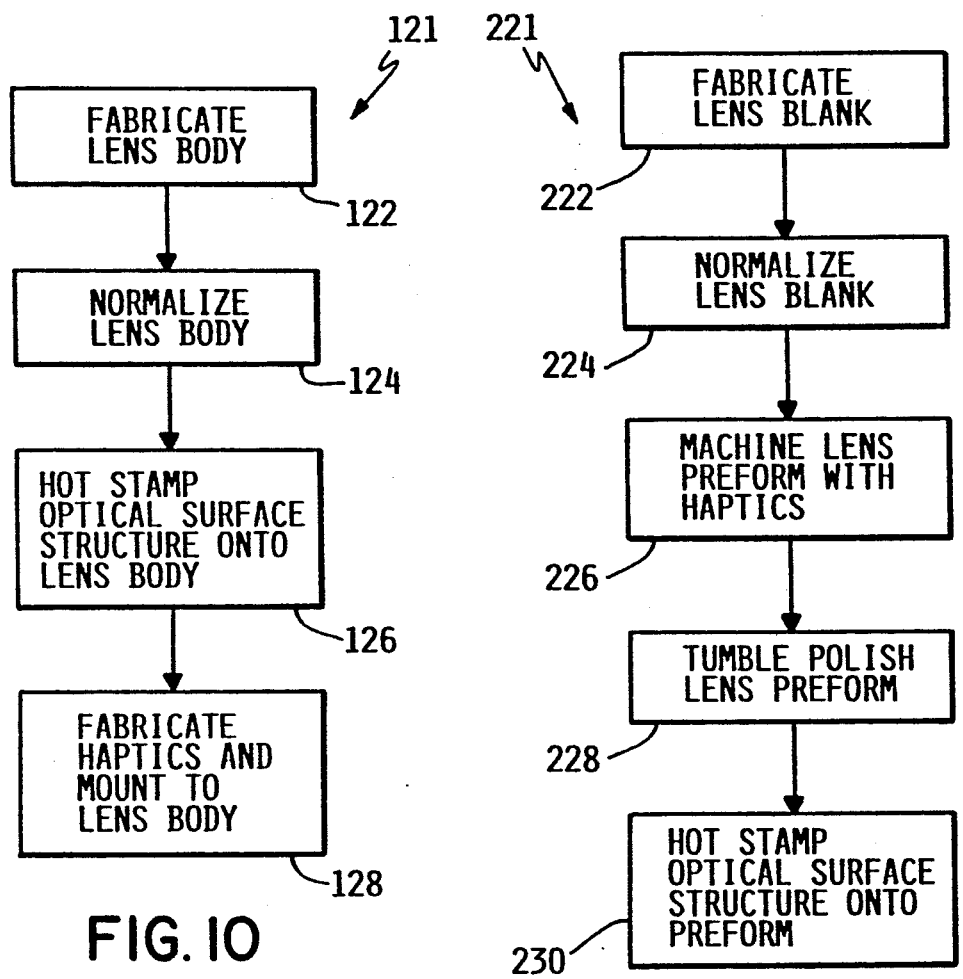
FIG. 10
FIG. 12
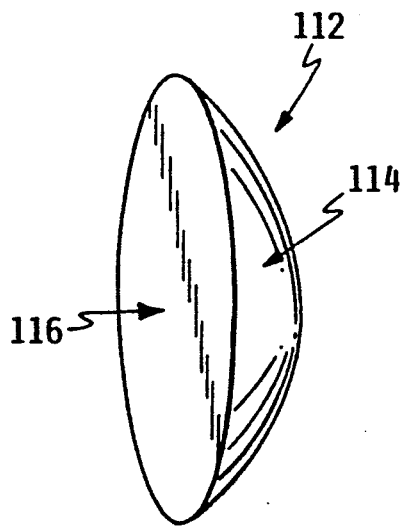
FIG. 11
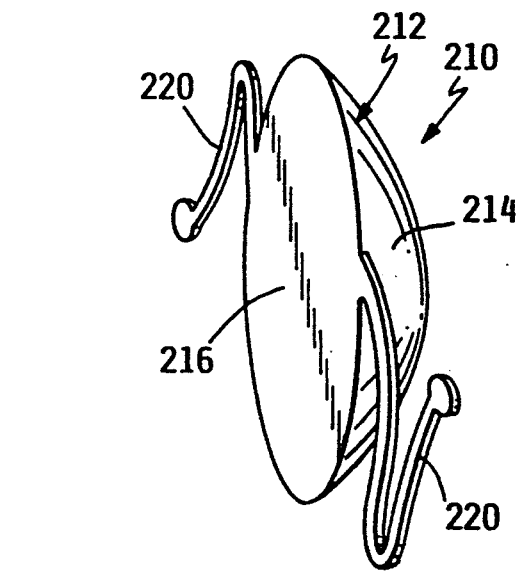
FIG. 13

METHOD OF HOT STAMPING INTRAOCULAR LENS BODIES

CROSS REFERENCE TO COPENDING APPLICATION

Reference is hereby made to commonly assigned copending application Ser. No. 07/456,680, filed Dec. 27, 1989, and entitled "Ultrasonically Welded Hydrogel Ophthalmic Lens".

FIELD OF THE INVENTION

The present invention relates generally to intraocular lenses and methods by which they are manufactured. In particular, the present invention is a hot stamping method for manufacturing intraocular lenses with surface structures on contoured lens areas.

BACKGROUND OF THE INVENTION

Intraocular lenses are used as surgically implanted replacements for damaged or diseased natural lenses in the human eye. Lenses of this type include a main lens element or body, and support elements known as haptics which hold the lens in position within the eye. The lens body is typically contoured with convex, concave and/or planar general overall shapes to provide refractive optical power. The contoured areas can have a smooth (i.e., single curve) optical surface. However, complex optical structures are often fabricated on the surfaces of the contoured areas to provide the lens with other optical powers and characteristics. Toric and aspheric lens structures and diffractive and refractive multifocal zone plates are examples of complex surface structures which can be found on intraocular lenses.

Multifocal lenses have several predetermined focal lengths to provide corrections for several ranges of vision (e.g., for driving and reading). These multifocal characteristics are provided by complex optical surface configurations. Lenses with multifocal diffractive zone plates use the principal of diffraction to provide the optical power. The use of multifocal diffractive zone plates in ophthalmic lenses is generally known and disclosed, for example, in the Cohen, U.S. Pat. Nos. 4,210,391, 4,338,005 and 4,340,283. Other lenses have complex surface configurations which utilize the principal of refraction to provide multifocal optical characteristics. Multi-curve multifocal ophthalmic lenses with spherical or aspherical sectors are disclosed in the Nordan U.S. Pat. No. 4,917,681, Nordan U.S. Pat. No. 4,769,033 and Nielson et al. U.S. Pat. No. 4,636,211. A multifocal lens with a spherical upper sector, a spherical middle sector and an aspherical lower sector is shown in the Nordan U.S. Pat. No. 4,917,681. The Shirayanagi U.S. Pat. No. 4,950,057 discloses a lens which includes a refractive multifocal Fresnel surface structure. Other known complex optical surface structures which use multiple zones to provide multifocal optics include the Achatz et al. U.S. Pat. No. 4,813,955, Frieder et al. U.S. Pat. No. 4,869,588, and Frieder et al. U.S. Pat. No. 4,952,048.

Intraocular ophthalmic lenses can be fabricated from a number of different polymer materials including polymethylmethacrylate (PMMA), silicone acrylate, perfluorinated polyethers, and hydrophilic materials such as hydrogels, polyurethanes and silicones. Perspex CQ (clinical grade) and CQ UV (with UV absorber) PMMA manufactured by Imperial Chemical Industries, PLC are especially good ophthalmic lens materials. Because of their extremely high molecular weight (measured in the range of 1.8M to 2.1M using a static low angle laser light scattering method (LALLS)), Perspex CQ and CQ UV offer a high degree of biocompatibility with the human body. Other desirable characteristics of these materials include their hardness, strength and optical quality. These materials are available only in cell-cast sheets.

Imperial Chemical Industries, PLC, the manufacturer of the Perspex PMMA referred to above, recommends that the cell-cast sheets be normalized in recirculating hot air ovens to relieve residual stress in the stock material. Normalization occurs when the cell-cast sheet is heated above its glass transition temperature and cooled under controlled conditions. During normalization, the Perspex sheet will shrink approximately two percent longitudinally and increase proportionately in thickness. However, the normalization treatment may cause depolymerization of the Perspex, and the oxygen can inhibit any re-polymerization, therefore degrading the material.

Intraocular lenses are often machined from lens members such as preformed buttons or semi-finished lens blanks. These buttons and blanks can be machined, sawed or punched from stock polymer material, or individually molded using injection, compression or casting techniques. The semi-finished lens blanks typically have one or more contoured areas. Following the formation of the multifocal diffractive zone plate or other surface structure on the appropriate portion of the lens blank, remaining portions of the blank are machined away. The lens can then be polished using techniques such as tumble polishing to remove any remaining surface roughness.

Mechanical machining methods are typically employed to impart the multifocal diffractive zone plate or other surface structure onto the surface of the lens member. This manufacturing technique has a number of disadvantages. Diamond tool turning of PMMA stock does not yield a satisfactory finish. Subsequent polishing of the machined surface structures is therefore required. However, polishing can detrimentally affect the optical characteristics of the machined surface structures. The optical surface structures are very minute (e.g., several dozen curved echelons 1-5 microns high in a diffractive zone plate), and must be machined to very close tolerances. Expensive equipment requiring skilled operators is therefore needed. These characteristics also make part-to-part reproducibility very difficult and necessitate expensive inspection procedures. Furthermore, it is especially difficult to machine these optical structures on concave or convex contoured surfaces. All of these factors add to the cost of diffractive multifocal ophthalmic lenses.

Intraocular lenses with complex surface structures can also be cast or molded as shown, for example, in the Bissonette et al. U.S. Pat. No. 4,753,653. However, these techniques have a number of disadvantages. Materials used to injection mold lenses are generally less desirable in that they have lower molecular weights and are not as hard. Voids or particulates are often present in molded lenses and exhibit refractiles which degrade the optical characteristics. Injection molded lenses also tend to be less dimensionally faithful to the tool because of warpage caused by variations in the density and location of the mold gate. The fidelity of tool replication can also be compromised by other aspects of the molding process such as venting and ejection.

Intraocular lens haptics can be molded or machined as a one-piece structure along with the optical portion of the lens, as shown in the Bissonette et al. patent referred to above. In other lenses such as those shown in the Chase et al. U.S. Pat. No. 4,242,761, Kaplan et al. U.S. Pat. No. 4,668,446 and Knoll et al. U.S. Pat. No. 4,936,849, the haptics are manufactured as separate members and subsequently attached to the lens. Of course the more time and effort that is required to manufacture and assemble the haptics, the more expensive the resulting intraocular lens.

It is evident that there is a continuing need for improved methods for manufacturing polymer intraocular lenses. Specifically, a relatively inexpensive, efficient and high precision method is needed.

SUMMARY OF THE INVENTION

The present invention is a relatively inexpensive and high precision method for manufacturing an intraocular lens from a polymer lens member. The lens member can be a blank or other preform, and has a lens generation area with a surface. The lens generation area is contoured to correspond to the desired contour of the finished lens. The method includes providing a stamping die having an optical embossing surface contoured as a physical negative of the lens generation area and bearing a physical negative of desired optical surface structure of the lens. The embossing surface of the stamping die and the surface of the lens member are forced into engagement with one another at a predetermined stamping pressure and for a predetermined stamping dwell time. Sufficient energy is applied to heat the surface of the lens member to a temperature above the glass transition temperature but below the melt temperature of the lens member. The optical surface structure is thereby embossed onto the surface of the lens generation area. The embossing surface of the stamping die is removed from the lens member following the expiration of the stamping dwell time.

In a preferred embodiment, the lens member is machined from a cell cast sheet of PMMA to a precompensated size larger than desired to compensate for normalizing shrinkage. The lens member is normalized by heating it within a vacuum oven. The optical embossing surface and/or the lens member are contoured to contact one another at the center of the surface of the lens member, and to have an area of contact which extends progressively outwardly in a radial direction as the die and lens member are engaged. This arrangement facilitates gas venting as the optical embossing surface is forced into engagement with the surface of the lens member.

Simple or complex optical surface structures can be embossed onto the lens generation area using this method. In one embodiment, the stamping die includes a physical negative of a multifocal diffractive zone plate. Other embodiments include the use of a stamping die bearing a physical negative of a toric lens surface.

In other embodiments the lens member also includes a contoured haptic generation area about the periphery of the lens generation area. The stamping die further includes a peripheral haptic embossing surface contoured as a physical negative of the haptic generation area and bearing a physical negative of desired haptic structure of the lens. Optical surface structure and haptic structure are embossed onto the surfaces of the lens member. Polymer material is machined from the lens member to produce a completed lens. The lens can also be polished to remove remaining surface roughness.

DESCRIPTION OF THE FIGURES

FIG. 10 is a flow chart generally describing a second embodiment of the method of the present invention.

FIG. 11 is an illustration of a lens member used to manufacture lenses in accordance with the method illustrated in FIG. 10.

FIG. 12 is a flow chart generally describing a third embodiment of the method of the present invention.

FIG. 13 is an illustration of a lens preform member fabricated in accordance with the method illustrated in FIG. 12.

DETAILED DESCRIPTION OF THE PREFERRED EMBODIMENTS

Figure 1:
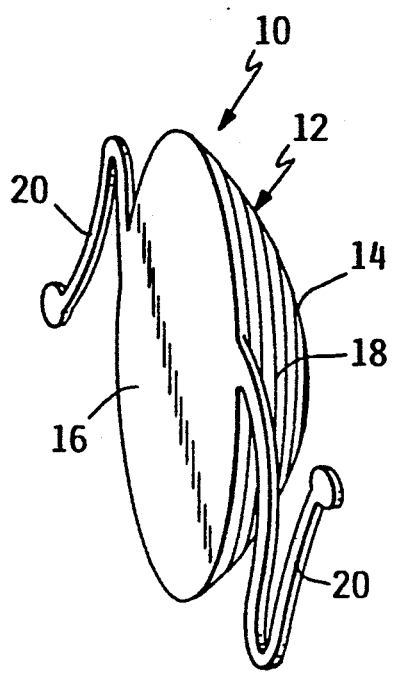
FIG. 1 is an illustration of a diffractive multifocal intraocular lens which can be manufactured in accordance with the method of the present invention.

An intraocular lens 10 manufactured in accordance with the present invention is illustrated generally in FIG. 1. In the embodiment shown, lens 10 is a plano-convex lens having a body 12 which has a first convex surface 14 and a second planar surface 16. An optical surface structure such as multifocal diffractive zone plate 18 is formed on body 12, and is shown on convex surface 14 in FIG. 1. Intraocular lenses such as 10 are designed to be surgically implanted, and include haptics 20. The diameter of body 12 of lens 10 is typically in the range of 5.0 to 7.5 mm, but can vary from this range as required for any particular application. Although lens 10 is shown with a circular profile, it can be provided with other shapes (e.g., oval).

Figure 2:
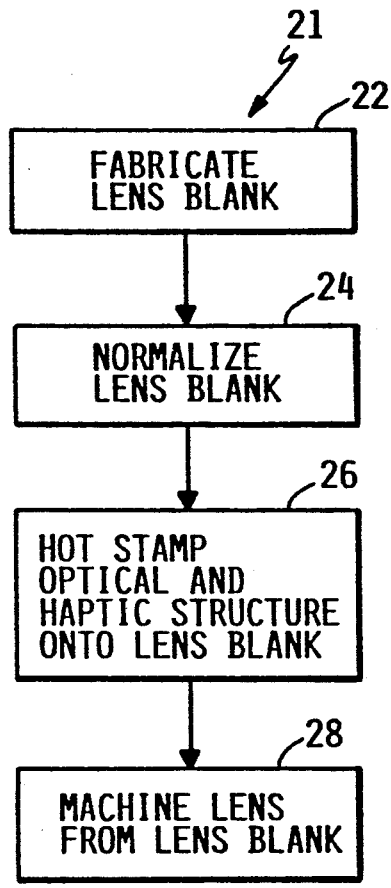
FIG. 2 is a flow chart generally describing the intraocular lens manufacturing method of the present invention.

Method 21, one embodiment of the method by which lens 10 can be manufactured in accordance with the present invention, is illustrated generally in FIG. 2. Manufacturing method 21 begins with lens blank fabrication step 22 during which a lens generation area and haptic generation area are contoured to their desired general shape in finished lens 10. The lens blank is then normalized at step 24. Normalization step 24 is a heating process which eliminates any remaining chemical instabilities and residual stress in the fabricated lens blank. Following normalization step 24, optical surface structures such as multifocal diffractive zone plate 18 and structural portions of haptics 20 are hot stamped onto the associated contoured areas of the lens blanks. Hot stamping involves the use of a stamping ram which bears a physical negative of the desired optical surface and haptic structures. The optical surface and haptic structures are embossed onto the surfaces of the lens blank by forcing the ram into engagement with the surfaces and applying heat. The finished lens is machined from the lens blank as illustrated by step 28. The lens can also be polished (e.g., tumble polished) to remove any remaining roughness from the machined surfaces.

Figure 3:
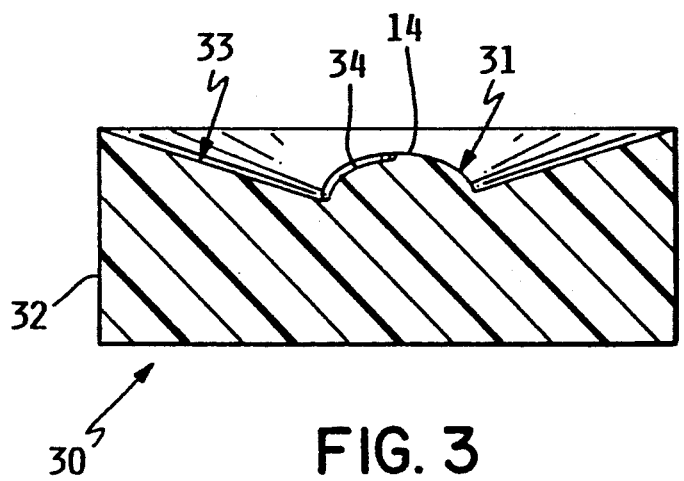
FIG. 3 is an illustration of a lens blank which can be used to manufacture intraocular ophthalmic lenses in accordance with the present invention.

A lens member such as blank 30 representative of that which can be produced during fabrication step 22 is illustrated generally in FIG. 3. Lens blank 30 is subsequently processed to fabricate a plano-convex lens 10 such as that illustrated in FIG. 1. For this reason, common reference numerals are used in FIG. 3 to identify those portions of lens blank 30 which correspond to the structure on completed lens 10. Lens blank 30 is a one-piece, flattened, cylindrical button or base 32 with a central lens generation area 31 from which the lens body such as 12 is ultimately taken. A haptic generation area 33 from which haptics 20 are ultimately taken extends around the periphery of lens generation area 31 in the embodiment shown.

Lens blank 30 is pre-shaped or semi-finished by providing lens generation area 31 and haptic generation area 33 with contours or general overall shapes which correspond to the contours of the associated portions of completed lens 10. For purposes of fabricating lens 10, blank 30 is imparted with a convex lens generation area 31 and a haptic generation area 33 which slopes upwardly with increasing distance from the lens generation area. A gas release structure such as vent groove 34 can be formed in the surface 14 of lens generation area 31 to facilitate hot stamping operation 26 in a manner described more completely below. Areas 31 and 33 are preferably contoured to such an extent that surface structures such as zone plate 18 and haptics 20 can be completely formed thereon with a minimum of polymer displacement. Although lens blank 30 includes a convex lens generation area 31 and a sloping haptic generation area 33, it is to be understood that other, differently contoured areas such as 31 and/or 33 can be imparted to the blank as needed for given applications. By way of example, blanks such as 30 can be preshaped with planar or concave contoured areas 31 or vaulted areas 33.

Lens blank 30 can be injection or compression molded from any of a wide variety of thermoplastic polymer materials. However, high molecular weight Perspex brand PMMA is the preferred material for fabricating lens blank 30, and is commercially available from Imperial Chemical Industries, PLC, only in cell cast sheets. Lens blanks 30 fabricated from Perspex PMMA must therefore be machined from the cell cast sheet. Machining techniques for fabricating lens blank 30 in accordance with step 22 are generally known. Since surface structures such as zone plate 18 are subsequently imparted to lens generation area 31 during hot stamping procedure 26, surface 14 need not be manufactured to a close tolerance, optical quality finish. The dimensions to which lens blank 30 is machined or otherwise fabricated are precompensated to accommodate expected shrinkage during normalization procedure 24. Perspex PMMA sheets shrink approximately two percent longitudinally during normalization operation 24. In one embodiment lens body 12 is machined to a diameter of 0.7643 inch (19.413 mm) so it will have the desired diameter of 0.7480 inch (19 mm) following normalization. As described below, the dimensions of the lens generation area surface 31 can also be configured to facilitate the evacuation of gases during hot stamping operation 26.

Normalization procedure 24 can begin by washing lens blank 30 in a mild detergent and water. The washed lens blank 30 should be thoroughly rinsed with deionized water to remove any remaining debris or other substances. Sterile water can be used for the final rinse.

Normalization procedure 24 is continued by placing the washed and rinsed lens blank 30 on a clean base (not shown) which has been coated or covered with a surface tension reducing material (not shown). A glass sheet can be used for the base. The surface tension reducing material prevents lens blank 30 from sticking to the glass sheet, and should therefore have a low surface tension. The surface tension reducing material should also have a number of other properties. This material should not physically deteriorate or evolve any chemicals or gasses when heated, to prevent contamination of lens blanks 30 during normalization procedure 24. For similar reasons, the material should be of known composition and particulate free. Spun glass or filtration materials such as #541 and GF/A manufactured by the Whatman Paper Co. of Dover, N.J., U.S.A., can be used for this purpose.

The glass tray bearing the lens blank 30 is placed in a vacuum oven (not shown) for a heating cycle. To prevent contamination, the vacuum oven should be meticulously cleaned before the tray is placed therein, and subsequently purged with nitrogen or other dry gas. In one embodiment the vacuum oven is purged twice by evacuating it to a pressure of at least twenty five inches (63.5 cm) Hg before being vented to atmospheric pressure with dry nitrogen. The loaded oven is evacuated to at least twenty five inches Hg before being subjected to the heat cycle. The heat cycle to which the lens blank 30 is subjected in one embodiment of the invention is specified on the following chart.

| NORMALIZATION HEATING CYCLE SEQUENCE | | |
|---|---|---|
| Time Period | Temperature Change | Rate of Temperature Change |
| 30 Minutes | Ambient to 125° C. | Approx. 200° C./Hr. |
| 30 Minutes | 125° C. to 140° C. | 30° C./Hr. |
| 2 Hours | 140° C. | — |
| 4 Hours | 140° C. to 104° C. | 9° C./Hr. |
| 4 Hours | 104° C. | — |
| 18 Hours | 104° C. to 32° C. | 4° C./Hr. |

Upon completion of the heating cycle the oven is cooled to ambient temperature but maintained under vacuum until it is to be unloaded. The vacuum can be released by the introduction of dry nitrogen into the oven. After the heating cycle lens blank 30 is transferred, preferably in an anaerobic environment, to a particulate-free dry storage container having a low vapor transmission rate. Lens blank 30 can be stored in this container until the initiation of hot stamping procedure 26. However, it can be advantageous to immediately initiate hot stamping procedure 26 to help prevent contamination of lens blank 30. In other embodiments, lens blank 30 can be cleaned, surface dried and preheated for hot stamping procedure 26 in a vapor phase condensation heating chamber. A perfluorinated fluid can be boiled to create the vapor for this cleaning, drying and preheating procedure.

The normalization procedure 24 described above offers a number of advantages. In addition to shrinking lens blank 30 to reduce residual stress and provide better long term stability, the lens blank is simultaneously dried. Additional heat history is therefore not required for drying. Use of the vacuum also enhances the removal of moisture and any free monomer which may be present in polymer lens blank 30 or liberated during the heating cycle. Oxygen enhanced degradation is also precluded since normalization procedure 24 is carried out in an anaerobic environment.

Figure 4:
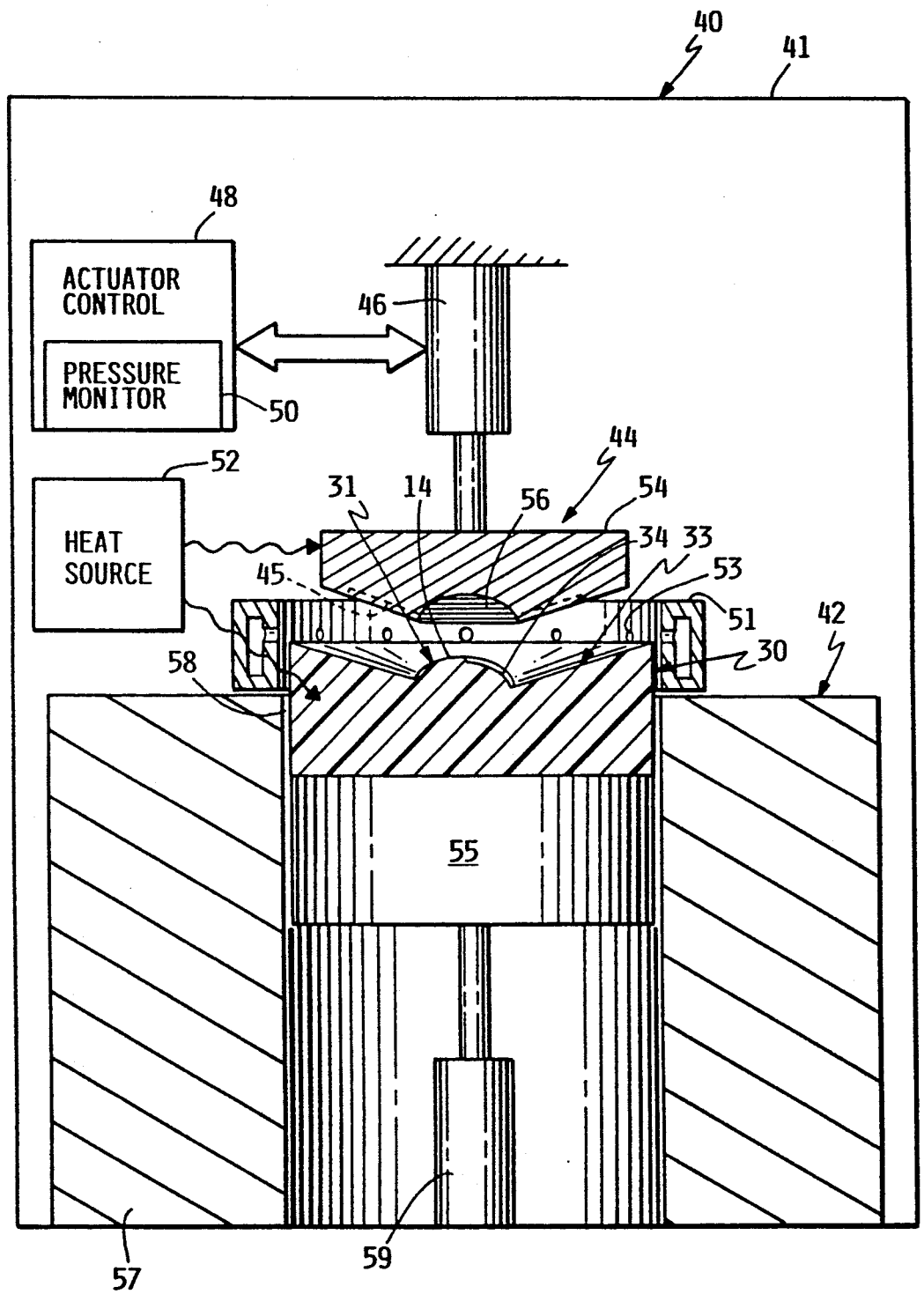
FIG. 4 is an illustration of a first embodiment of a hot stamping system which can be utilized in accordance with the present invention to manufacture intraocular lenses.

Hot stamping system 40, a first embodiment of equipment which can be used to implement hot stamping procedure 26 in accordance with the present invention, is illustrated generally in FIG. 4. Hot stamping system 40 includes a lens blank fixture 42 which is enclosed by chamber 41. In one embodiment, chamber 41 is an anaerobic chamber. Also mounted within chamber 41 is a pressure actuator such as first air cylinder 46, stamping ram 44, actuator control 48, pressure monitor 50, coolant plenum 51 and a heat source 52. Fixture 42 is a base which is configured to securely hold lens blanks such as 30 during hot stamping procedure 26. In the embodiment shown, fixture 42 includes base member 55 positioned within tubular member 57 to form a recess 58 which is sized to securely but releasably receive lens blank 30. Second air cylinder 59 drives base member 55 with respect to tubular member 57 to eject lens blank 30 from fixture 42.

Stamper ram 44 includes a die 54 with an optical surface structure embossing surface 56 and a haptic structure embossing surface 45 (shown in phantom) machined or otherwise formed thereon. Embossing surfaces 56 and 45 are contoured as physical negatives of lens generation area 31 and haptic generation area 33, respectively, so the embossing surfaces will mate with the corresponding generation areas. In the embodiment shown in FIG. 4 which is configured for use with blank 30, optical embossing surface 56 is concave while haptic embossing surface 45 slopes upwardly with increasing distance from the optical embossing surface. Optical surface 56 also includes a mirror image or physical negative of the optical surface structure such as diffractive multifocal zone plate 18 which it is desired to emboss onto the lens generation area 31 of lens blank 30. A physical negative of the haptic structure such as haptics 20 is similarly machined or formed into haptic embossing surface 45. In one embodiment stamper ram 44 is a contoured copper member on which a layer of high phosphorous nickel has been deposited. The optical embossing surface is machined onto the nickel layer to tolerances sufficient to impart an optical quality finish onto generation area 31 during hot stamping operation 26.

Thermal energy is transferred to lens generation area 31 of blank 30 during hot stamping procedure 26. The amount of energy transferred must be sufficient to heat the surfaces of lens generation area 31 and haptic generation area 33 to a temperature greater than or equal to the glass transition temperature (Tg) of the polymer from which lens blank 30 is fabricated, but less than the melt flow temperature of the polymer. The temperature to which lens blank 30 is heated is preferably a temperature less than that which will cause significant or otherwise unacceptable chemical or molecular degradation of the polymer material. Temperatures no greater than 100° C. above the glass transition temperature will generally meet these requirements.

In the embodiment of hot stamping system 40 shown in FIG. 4, heat source 52 is provided as the source of thermal energy. Heat source 52 can apply the requisite energy in one or more of several alternative manners. A first alternative is to use heat source 52 to directly heat lens generation area 31 and haptic generation area 33 of lens blank 30. Heat source 52 can also be used to heat fixture 42, in which case generation areas 31 and 33 would be indirectly heated through the fixture. In a third alternative, heat source 52 includes a coil (not shown) mounted to die 54. The thermal conductivity of embossing surfaces 56 and 45 is used to transfer heat to generation areas 31 and 33 from the coil. Lens blank 30 can also be preheated by a heat source such as 52 before it is positioned into chamber 40. Heat source 52 can be a conventional electrical resistance-type device.

Coolant plenum 51 is connected to a source of coolant fluid (not shown) and is used to cool die 54 and/or lens blank 30 during hot stamping procedure 26. In the embodiment shown, plenum 51 is a tubular ring positioned around recess 58 at the position at which die 54 and lens blank 30 are engaged. Apertures 53 through the inner surface of plenum 51 direct coolant fluid such as clean, dry nitrogen to die 54 and/or lens blank 30. In other embodiments (not shown) plenum 51 is a coolant receiving chamber within die 54.

Figure 6:
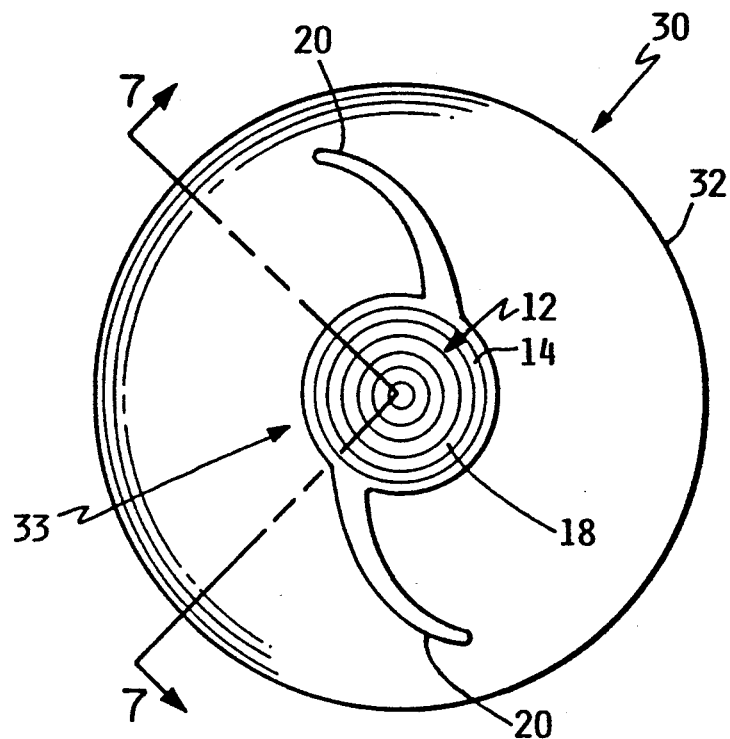
FIG. 6 is a top view of a lens blank such as that shown in FIG. 3 after it has been embossed.
Figure 7:
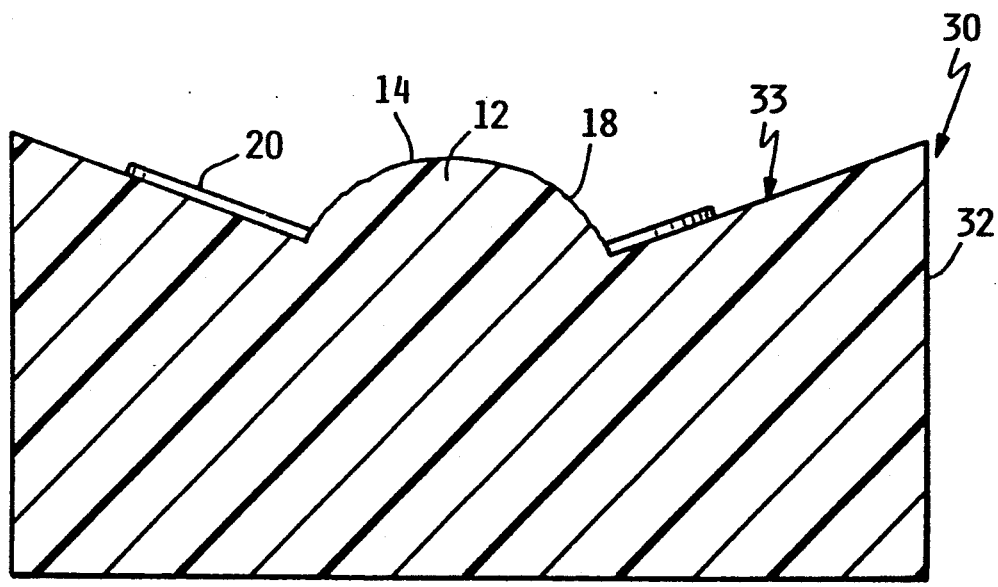
FIG. 7 is a sectional side view of the embossed lens blank shown in FIG. 6.

Air cylinder 46 provides relative motion to force die 54 into engagement with lens blank 30 during hot stamping procedure 26. Air cylinder 46 is controlled by actuator control 48 and causes die 54 to engage lens blank 30 at a predetermined stamping pressure and for a predetermined stamping dwell time. Pressure monitor 50 can be used to determine the amount of pressure applied between lens blank 30 and die 54. Die 54 and/or lens blank 30 can also be cooled during the dwell time. Following the expiration of the stamping dwell time, actuator control 48 causes air cylinder 46 to disengage die 54 from lens blank 30. Air cylinder 59 is actuated to eject lens blank 30 from fixture 42. Top and sectional side views of a lens blank 30 which has been hot stamped in accordance with procedure 26 are illustrated in FIGS. 6 and 7, respectively. Surface structures such as zone plate 18 and haptics 20 are retained within lens body 12 and haptic generation area 33, respectively, by residual stress after hot stamping procedure 26.

The temperature, pressure and dwell time parameters of hot stamping procedure 26 are optimized and balanced to impart an optical quality replication of the surface structures such as zone plate 18 and/or haptics 20 to the respective generation areas 31 and 33 of blank 30, while at the same time minimizing the amount of physical stress and heat history applied to the lens blank. One successfully implemented procedure 26 for hot stamping a multifocal diffractive zone plate 18 is performed at ambient room temperature (about 20° C. or 72° F.) in a clean bench with a 100 feet per minute flow of class 100 deionized air. Lens blank 30 was preheated to 65° C. over a 12 hour period. Die 54 (bearing only optical embossing surface 56 and not haptic embossing surface 45 in this embodiment) is heated to a temperature of 150°±3° C. (300°±5° F.) before it is engaged with lens blank 30 at a pressure of 4.5M Pascal (about 650 psi). This stamping pressure is maintained for a stamping dwell time of 30 seconds during which die 54 and lens blank 30 are cooled to a temperature of 93° C. (200° F.).

In other embodiments of procedure 26 for hot stamping zone plate 18, lens members 30 at room temperature were positioned on heated base member 55 for a time period of 0.2 to 2.5 minutes before engagement with die 54. The base member 55 is preheated to a temperature of 21°–60° C. (70°–150° F.). Die 54 is heated to a temperature of 177°–204° C. (350°–400° F.) before it is engaged with lens blank 30. Stamping pressures of 3.0 to 4.5M Pascals (433–650 psi) were used. The dwell time is 2.0–5.3 minutes, during which die 54 and base member 55 are cooled to a temperature of 60° C. (140° F.).

In general, as the temperature of die 54 is increased, the stamping pressure can be lowered. However, the dwell time may have to be increased to allow die 54 to cool sufficiently to enable the die to be removed from lens blank 30. It is evident that a wide range of parameters can be used.

Lens generation area 31 of blank 30 and/or embossing surface 56 of die 54 can be configured to prevent gas from becoming entrapped between the die and lens blank during hot stamping procedure 26. Any such trapped gasses could prevent the accurate reproduction of zone plate 18 onto lens generation area 31. In one embodiment, one or more vent grooves 34 fabricated on lens generation area 31 can prevent entrapment of gas by providing a release path for the gases. Vent groove 34 and die 54 must be configured in such a manner that the grooves 34 will be eliminated or filled in by the displacement of polymer lens material during hot stamping procedure 26.

Alternatively, or in addition to the use of vent grooves 34, the relative contour dimensions of die 54 and lens generation area 31 can be fabricated to ensure that the area of contact between optical embossing surface 56 and the surface 14 and groove 34 of lens blank 30 begins at a central point and progresses radially outwardly as the die continues to be forced into engagement with the lens generation area. In the embodiment shown in FIG. 4, for example, this action can be accomplished by contouring embossing surface 56 with a radius of curvature which is somewhat greater than the radius of curvature of lens generation area 31. This arrangement will enable all gases to travel outwardly, preceding the area of contact between die 54 and lens generation area 31 as the die is brought into engagement with the lens generation area.

Figure 5:
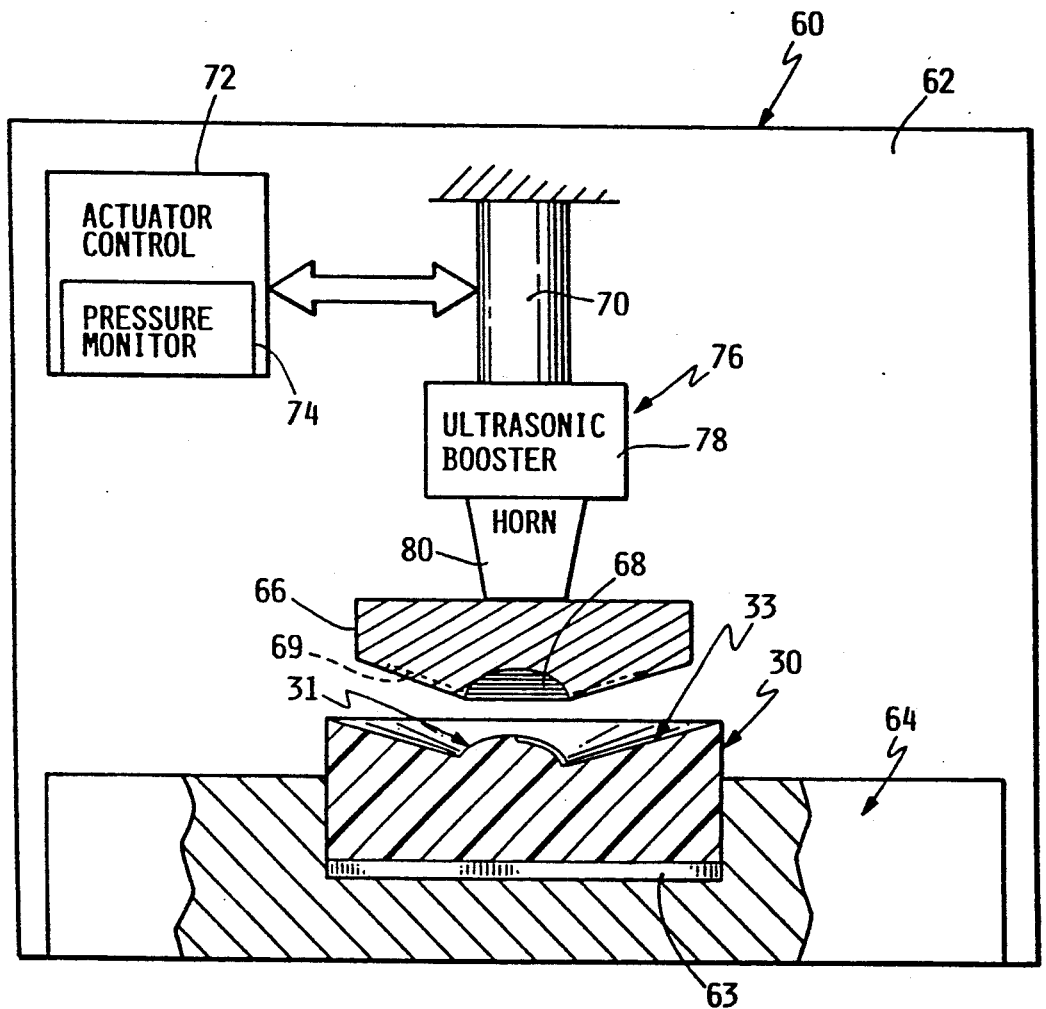
FIG. 5 is an illustration of a second embodiment of a hot stamping system which can be used to manufacture intraocular lenses in accordance with the present invention.

Hot stamping system 60, a second embodiment of the apparatus which can be used to implement hot stamping procedure 26, is illustrated in FIG. 5. Hot stamping system 60 includes an anaerobic chamber 62 which houses a lens blank receiving fixture 64, stamping die 66 with optical embossing surface 68 and haptic embossing surface 69, air cylinder 70, air cylinder control 72 and pressure monitor 74. These elements of hot stamping system 60 can be functionally identical to their counterparts in hot stamping system 40 described above with reference to FIG. 4. Although not shown, a coolant plenum such as that shown at 51 in FIG. 4 can also be mounted to fixture 64. However, hot stamping system 60 includes an ultrasonic welder 76 for generating the thermal energy required during hot stamping procedure 26. A thin flexible insert 63 can be inserted between fixture 64 and lens blank 30 to prevent surface structure on the base of the fixture from being transferred to the lens blank. An insert 63 of rubber or paper can be used for this purpose.

Ultrasonic welder 76 includes an ultrasonic booster 78 and a horn 80. In the embodiment shown in FIG. 5, stamping die 66 is mounted to horn 80. In alternative embodiments (not shown), ultrasonic welder 76 can be fixedly mounted, and an air cylinder (not shown) actuated to force fixture 64 and lens blank 30 into engagement with horn 80. Ultrasonic welder 76 can be a Branson Model 4AE welder. Ultrasonic energy produced by booster 78 is coupled to stamping die 66 by horn 80. A silver booster 78 which generates ultrasonic energy at a frequency of 40 KHz is used in one embodiment. Green and black (1:2.5 gain) boosters are used in other embodiments. The ultrasonic energy applied to stamping die 66 from welder 76 is converted to thermal energy to facilitate the high quality replication of optical embossing surface 68 and haptic embossing surface 69 onto lens generation area 31 and haptic generation area 33, respectively, during hot stamping procedure 26. In one hot stamping procedure utilizing system 60, the dwell time period during which die 66 and lens blank 30 are engaged is divided into a weld time period during which booster 78 is actuated, and a hold time period during which stamping pressure is still applied but booster 78 is deactivated.

Time and pressure parameters used to implement hot stamping procedure 26 with stamping system 60 can be varied to optimize the replication of embossing surfaces 68 and 69 onto blank 30. In one set of trials using a green booster 78, the best zone plate reproduction (no haptic embossing surface was formed on the stamping die) was achieved with a stamping pressure of 0.541–0.65M Pascals (78.5–94.3 psi) with a weld time period of 3.0 seconds and a hold time period of 1.0 seconds. Stamping pressures between 0.433M Pascals (62.8 psi) and 0.65M (94.3 psi) Pascals and weld time periods of 1.0 seconds to 3.0 seconds have also been utilized in stamping procedure 26 with a green booster 78, but resulted in lesser quality replication of embossing surface 68. In trials with a black booster 78, the best replication of surface 68 was achieved with a stamping pressure of 0.433M Pascals (62.8 psi), a weld time period of 400 to 500 msec, and a hold time period of 1.0 seconds. Lesser quality reproduction using a black booster 78 was observed when weld times were increased to 3.0 seconds.

Figure 18:
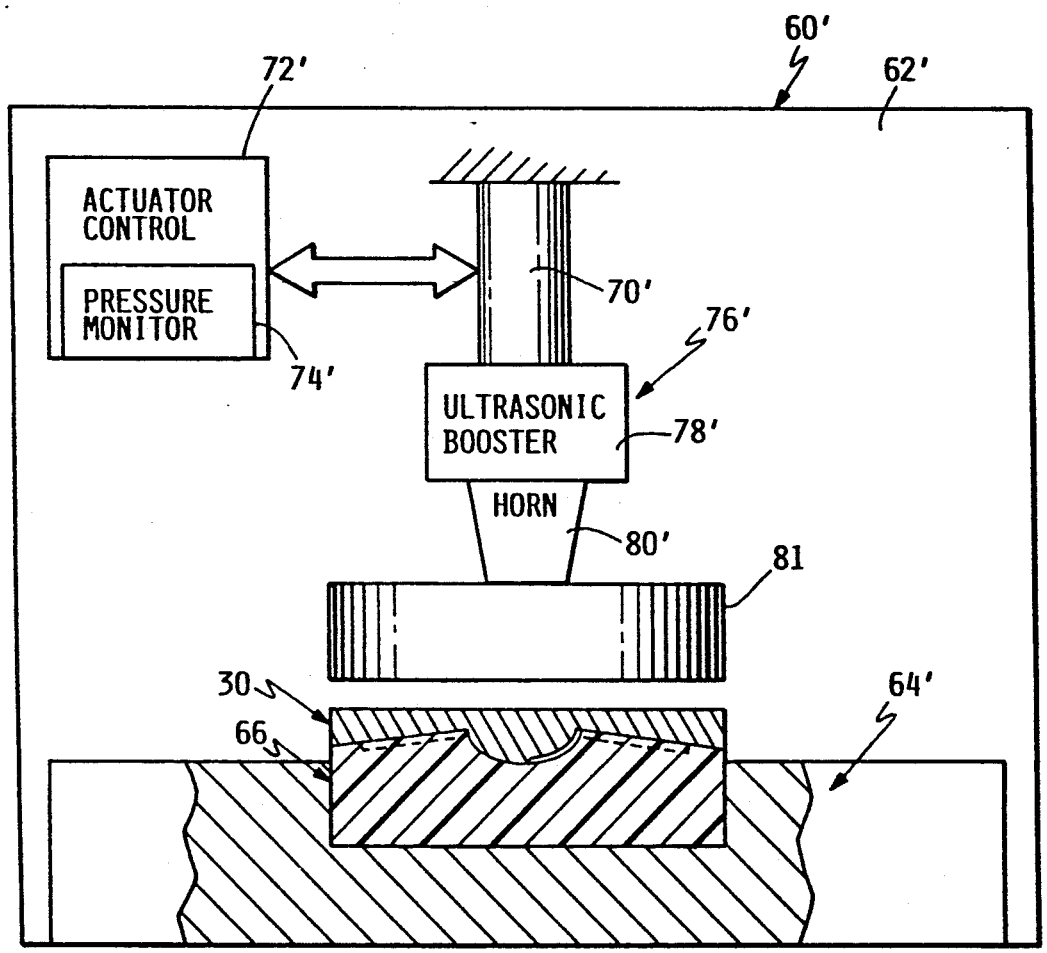
FIG. 18 is an alternative embodiment of the hot stamping system shown in FIG. 5

Hot stamping system 60', an alternative embodiment of system 60, is illustrated in FIG. 18. Common elements are identified with common, but primed (i.e., "'") reference numerals. As shown, in system 60' the stamping die 66 is mounted in blank receiving fixture 64'. Lens member 30 is placed on die 66. A tool 81 is mounted to horn 80', and is configured to engage lens member 30. When tool 81 is forced into engagement with lens member 30 and booster 78' activated, ultrasonic energy is transmitted through tool 81 and lens member 30 to the interface between the lens member and die 66.

Figure 8:
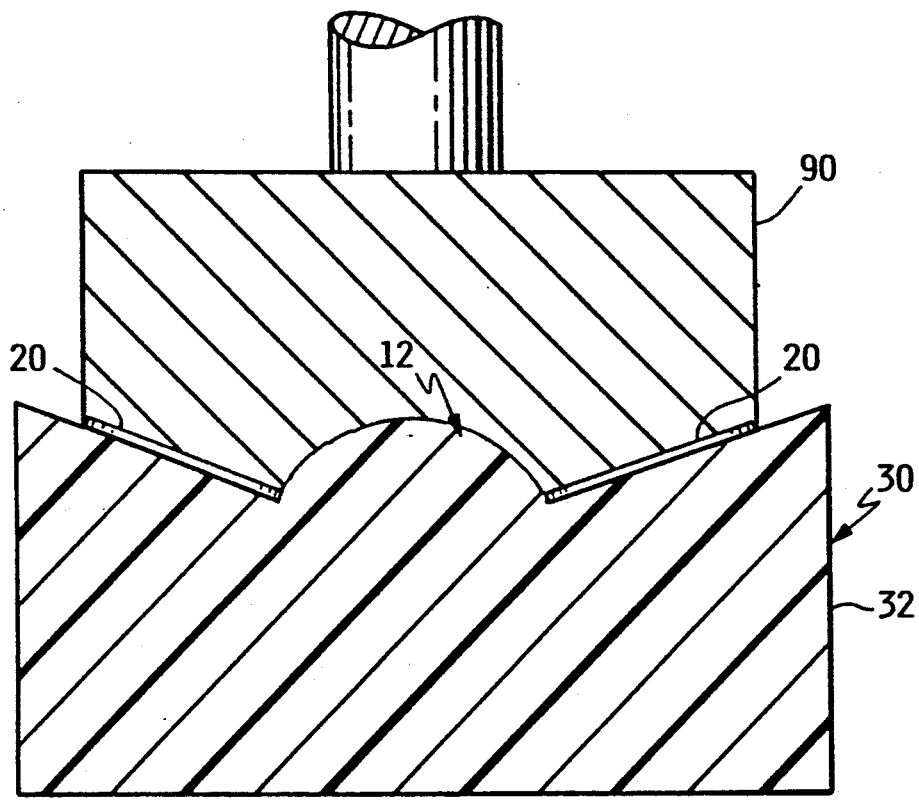
FIG. 8 is an illustration of the lens blank shown in FIG. 7 after it has been attached to a lathe mandrel.
Figure 9:
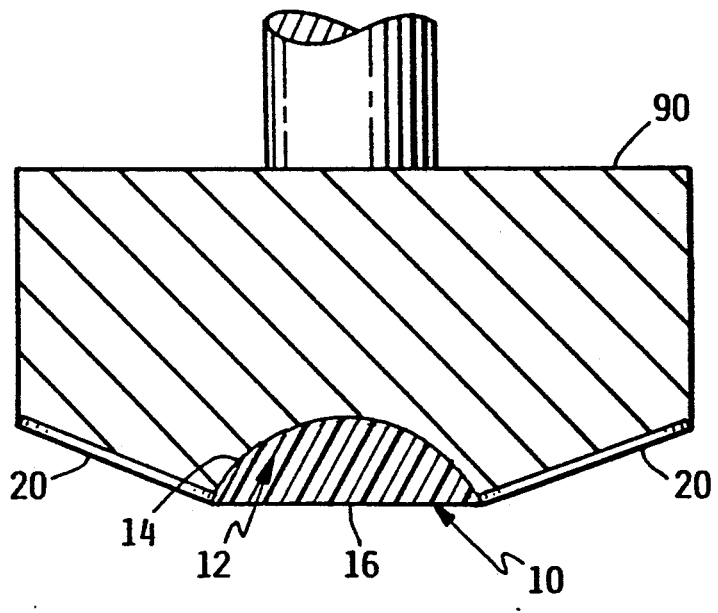
FIG. 9 is an illustration of a completed lens machined from the blank shown in FIG. 8.

As is illustrated generally by step 28 in FIG. 2, lenses such as 10 can be machined from blanks 30 after optical surface structures such as zone plate 18 and haptic structures such as 20 have been hot stamped onto the blank. One method for machining lens 10 from hot stamped blank 30 involves waxing the hot stamped surface of the blank to a lathe mandrel 90 as shown in FIG. 8. When mandrel 90 and blank 30 are rotated, portions of the blank on the side opposite the mandrel can be removed to produce lens surface 16 and expose haptics 20. A lens 10 which has been machined from blank 30 in accordance with step 28 but is still attached to lathe mandrel 90 is shown in FIG. 9. Machining step 28 can also be performed using other known or conventional techniques. Lens 10 can be polished using known procedures (e.g., tumble polishing) to eliminate any roughness on the machined surfaces.

Figure 14A:
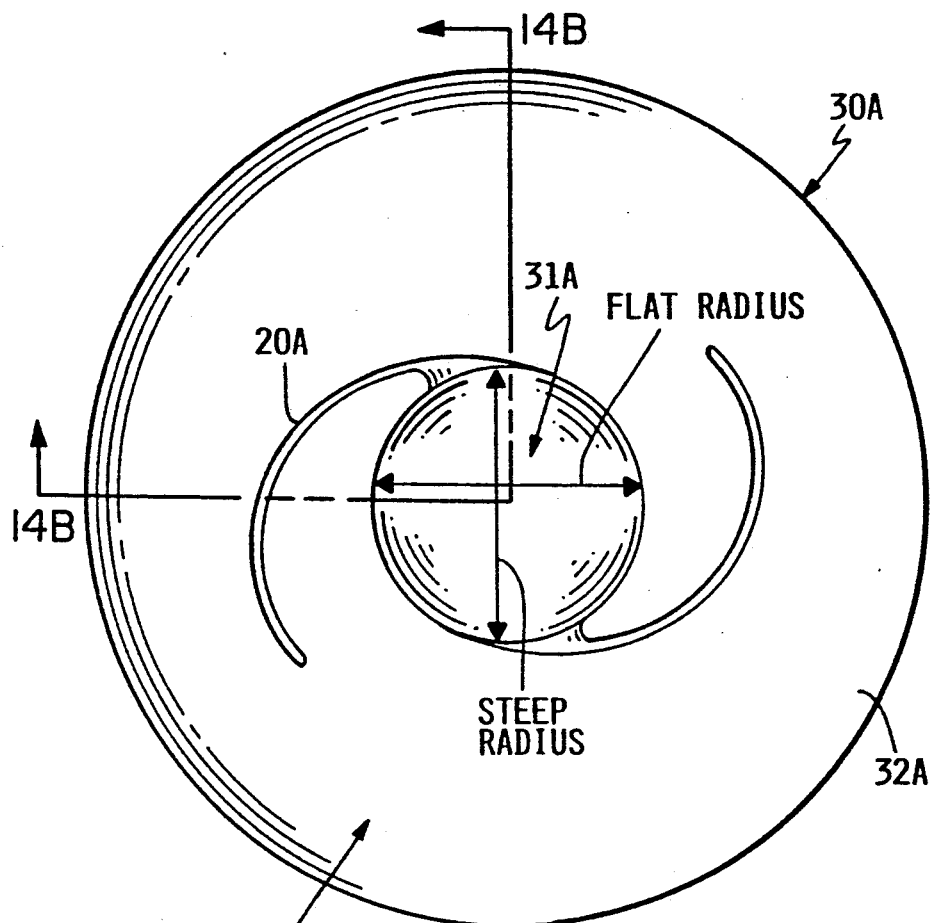
FIG. 14A is a top view of a lens blank embossed with a toric optical surface.
Figure 14B:
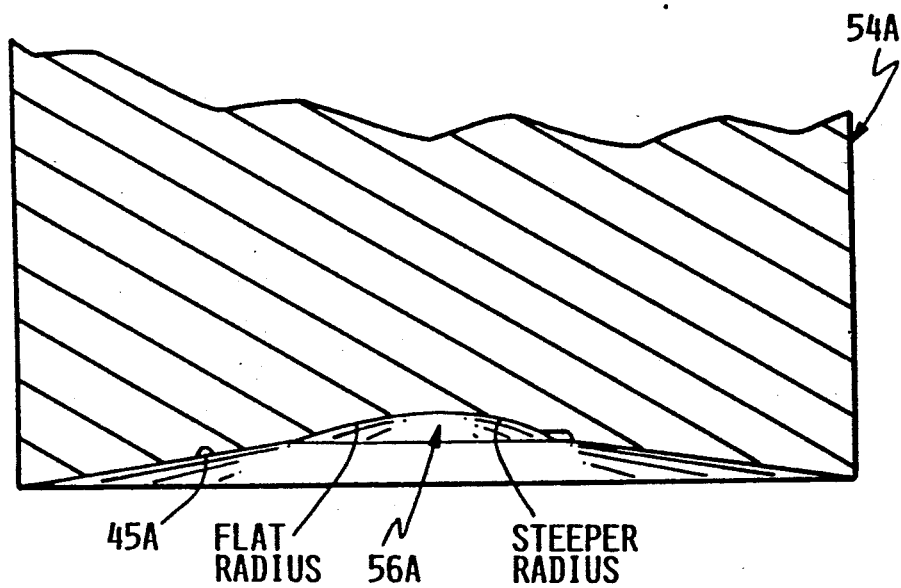
FIG. 14B is an orthogonal sectional view (corresponding to the section lines in FIG. 14A) of a stamping die with a toric embossing surface for producing a lens blank such as that shown in FIG. 14A.

Although optical embossing surface 56 of die 54 includes a multifocal diffractive zone plate for fabricating lenses such as 10 in the embodiment described above, it is to be understood that other complex optical surface structures and simple optical surface structures can be formed onto the embossing surface and imparted to the lens. By way of example, a lens blank 30A having a toric surface structure hot stamped onto its lens generation area 31A is illustrated in FIG. 14A. A cross section of die 54A having a toric embossing surface 56A for fabricating blank 30A is shown in FIG. 14B. The radii of curvature, of both the hot stamped lens generation area 31A and toric embossing surface 56A, differ from one another along the perpendicular (orthogonal) section lines shown in FIGS 14A and 14B. This toric property is depicted by the relatively flat and steep radii in FIGS. 14A and 14B. Other features of blank 30A and die 54A can be similar to their counterparts described above, and are identified by identical reference numerals with the suffix "A".

Figure 15A:
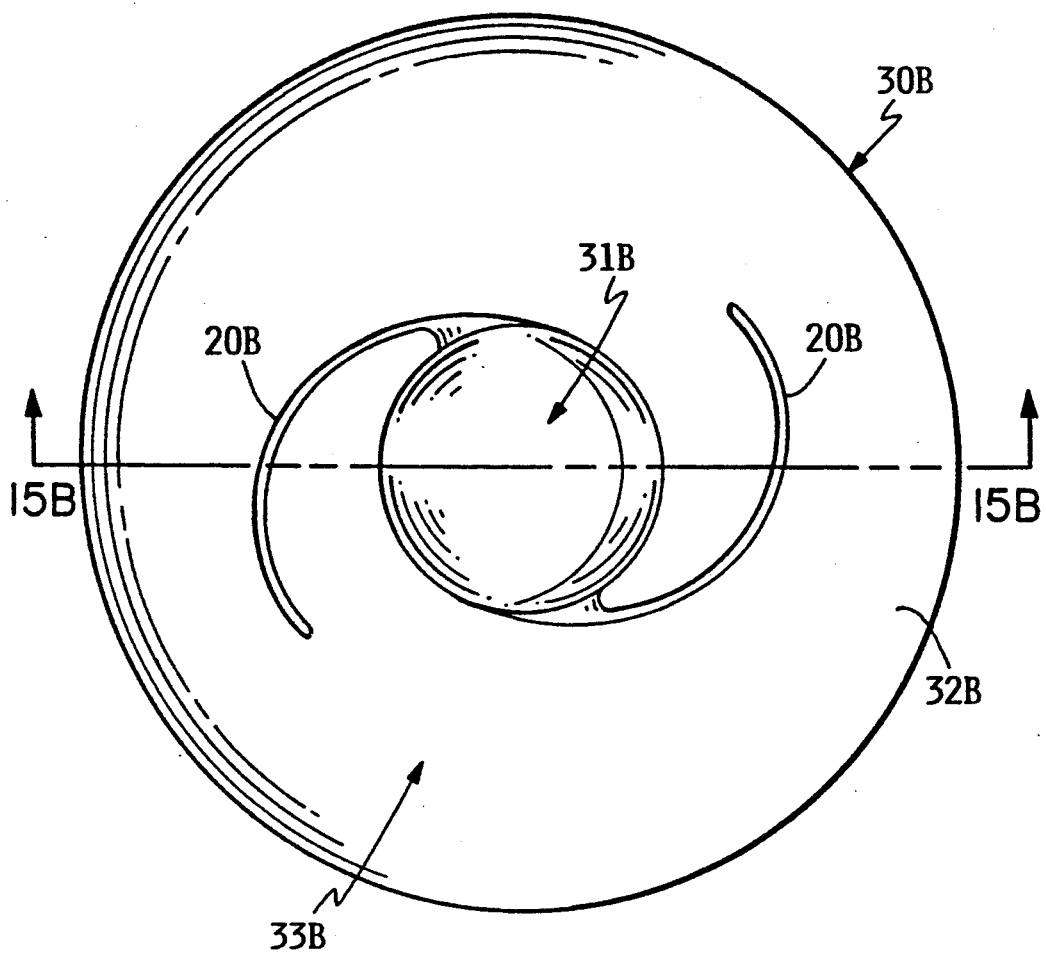
FIG. 15A is a top view of a lens blank embossed with an aspheric multifocal optical surface structure.
Figure 15B:
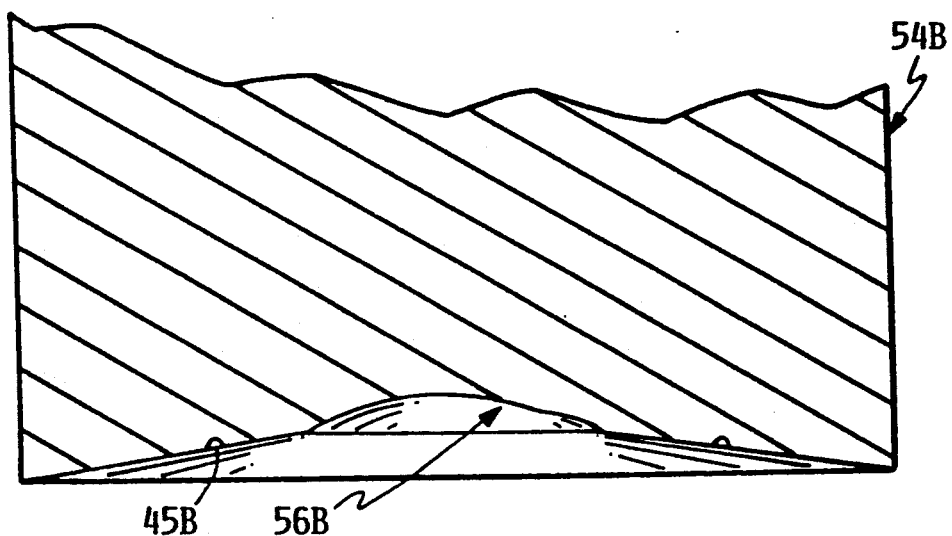
FIG. 15B is a sectional view of a stamping die with an aspheric multifocal optical structure for producing a lens blank such as that shown in FIG. 15A.
Figure 16A:
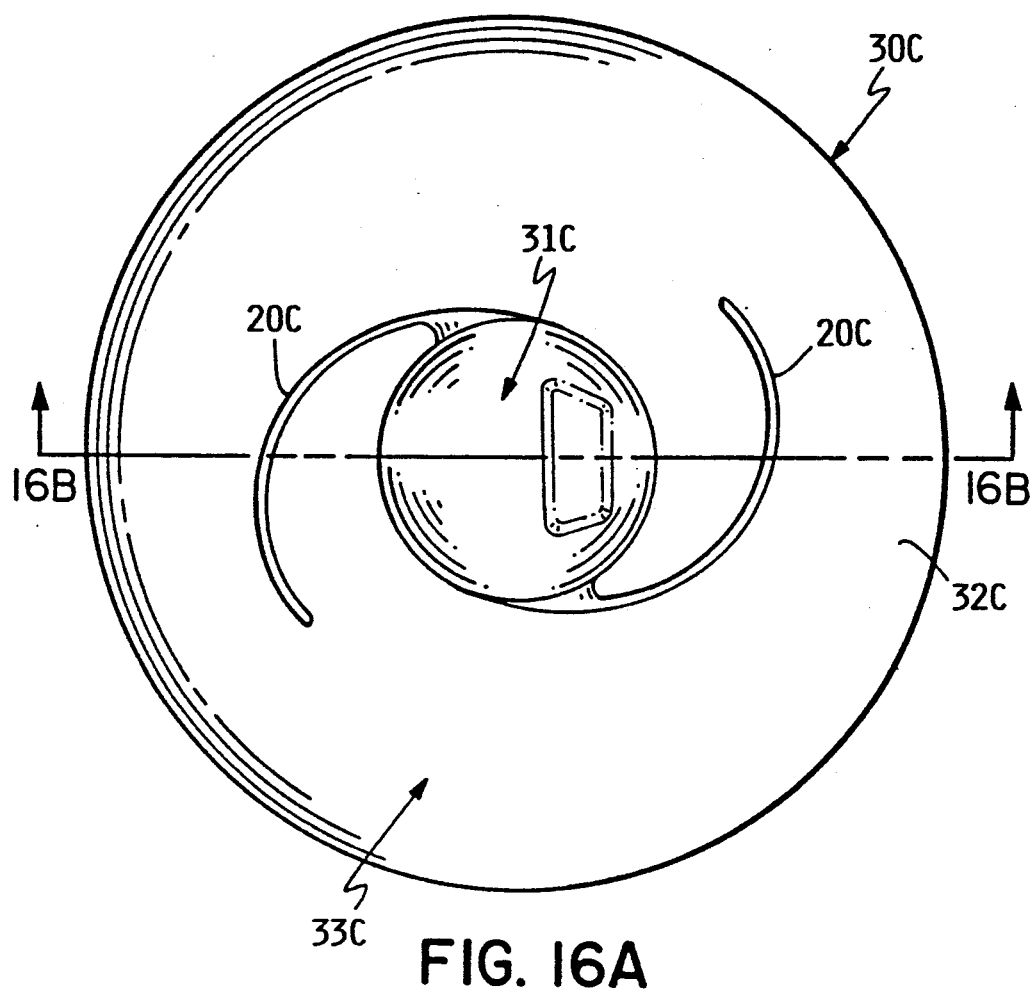
FIG. 16A is a top view of a lens blank embossed with a multiple spherical surfaced multifocal optical surface structure.
Figure 16B:
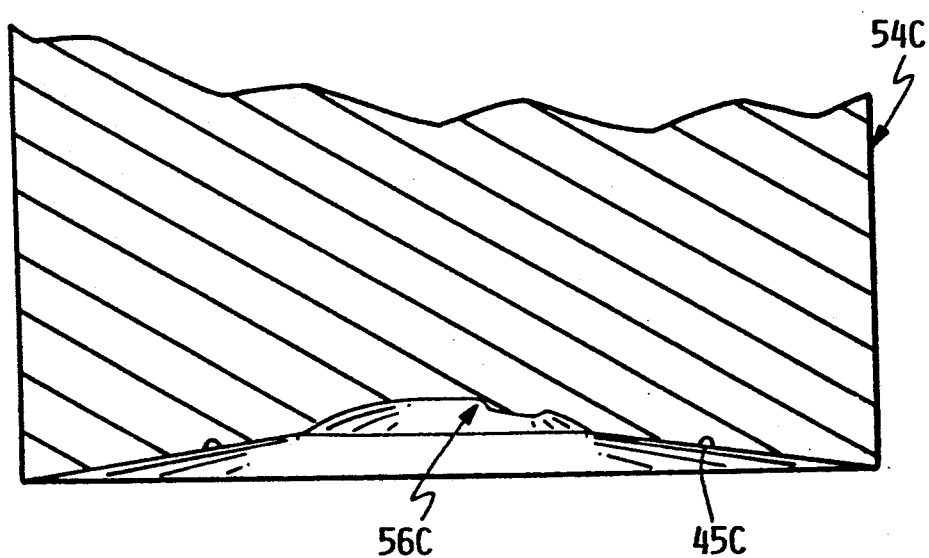
FIG. 16B is a sectional view of a stamping die with a multiple spherical surfaced multifocal optical structure for producing a lens blank such as that shown in FIG. 16A.
Figure 17A:
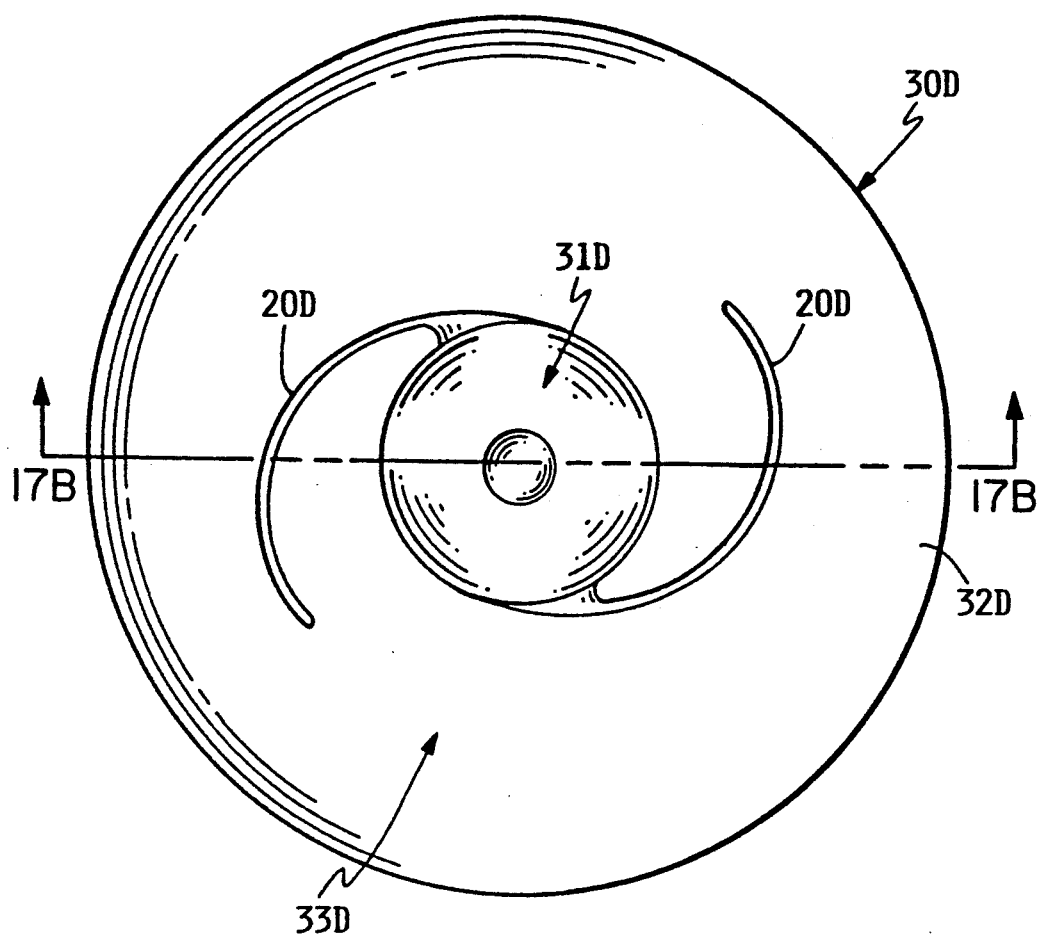
FIG. 17A is a top view of a lens blank embossed with a multiple curved multifocal optical surface structure.
Figure 17B:
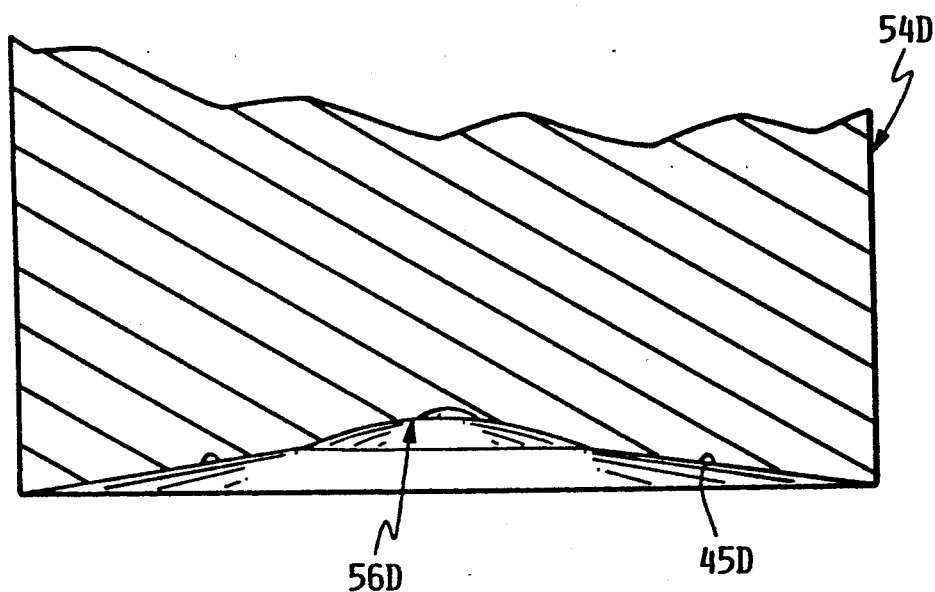
FIG. 17B is a sectional view of a stamping die with a multiple curved multifocal optical surface structure for producing a lens blank such as that shown in FIG. 17A.

A lens blank 30B having an aspheric multifocal optical structure hot stamped onto its lens generation area 31B is illustrated in FIG. 15A. A cross section of die 54B having an aspheric multifocal embossing surface 56B for fabricating blank 30B is shown in FIG. 15B. A lens blank 30C having a multiple spherical surfaced multifocal optical structure, and a die 54C for fabricating the blank, are shown in FIGS. 16A and 16B, respectively. A multiple curved multifocal hot stamped lens blank 30D and a die 54D for fabricating the blank are shown in FIGS. 17A and 17B, respectively. Again, other features of these lens blanks and dies can be similar to their counterparts described above, and are identified with identical reference numerals with different suffixes.

Method 121, a second embodiment of the method by which lenses can be manufactured in accordance with the present invention, is illustrated generally in FIG. 10. Method 121 begins with the fabrication of a lens member such as unfinished lens body 112 shown in FIG. 11. Lens body 112 is a plano-convex member in the embodiment shown, and is contoured to include a convex lens generation area 114 and a planar lens generation area 116. Lens body 112 does not include haptics, but can be otherwise fabricated in a manner similar to that of lens blank 30 described above with reference to step 22 of method 21. Lens body 112 can be normalized following its fabrication, as shown at 124 in FIG. 10. Normalizing procedure 124 for lens body 112 can be identical to the normalizing procedure 24 for lens blank 30 described above. In other embodiments (not shown) lens body 112 is machined from a blank such as that shown in FIG. 3 which has been normalized in accordance with previously described procedure 24.

Optical structures such as those described above are hot stamped onto either or both of lens generation areas 114 and 116 as indicated by step 126. Hot stamping step 126 for lens body 112 can be performed in a manner similar to the hot stamping step 26 of lens blank 30 described above. Haptics (not shown) are manufactured and mounted to lens body 112 using known or conventional techniques as shown by step 128.

Method 221, another embodiment of the method by which lenses can be manufactured in accordance with the present invention, is illustrated generally in FIG. 12. Method 221 begins with the fabrication of a lens blank as shown at step 222. The lens blank (not shown) can be a flat cylindrical member fabricated from materials and in manners similar to those of lens blank 30 described above with reference to step 22 of method 21 However, no contoured lens generation areas or haptic generation areas need be provided. Following its fabrication, the lens blank is normalized as shown at 224 in FIG. 12. Normalizing procedure 224 can be identical to the normalizing procedure 24 for lens blank 30 described above.

After normalization procedure 224, an unfinished lens preform member 210 such as that illustrated in FIG. 13 is machined from the lens blank. This machining step is illustrated generally at 226 in FIG. 12. Lens member 210 is a one-piece member including body 212 and haptics 220. Lens body 212 includes a first surface 214 and a second surface 216, both of which are contoured in a convex manner in the embodiment shown. Lens member 210 can be machined from the blank using techniques similar to those described with reference to method 21 (FIG. 2). After lens member 210 is fabricated in this manner, it is tumble polished as shown at step 228 to remove any surface roughness caused by machining. Although body 212 will also be polished during step 228, the primary purpose of this polishing step is to provide haptics 220 with an implantable quality finish.

Complex and/or simple optical surface structures such as those described above are hot stamped onto surfaces 214 and 216 of lens member 210 as shown at 230 in FIG. 12. Hot stamping systems similar to those described above with reference to FIGS. 4 and 5, as well as associated procedures, can be used to implement step 230. Dies 54 and 66 of stamping systems 40 and 60, respectively, are configured in a manner (e.g., with reduced diameter) which prevents engagement with haptics 220 while lens member 210 is being hot stamped. Systems 40 and 60 can also be configured in a manner (not shown) with two stamping dies to enable simultaneous hot stamping of both 214 and 216. Surfaces 214 and 216 can include gas vent grooves and/or be sized with respect to the associated stamping dies to facilitate gas venting during hot stamping step 230.

The lens fabrication method described herein offers a number of important advantages. Expenses associated with the precision machining operations required to machine the optical surface structures and haptics onto intraocular lenses can be reduced. Part-to-part reproducibility in the multifocal zone plates or other optical structures is greatly enhanced, thereby simplifying inspection procedures. The surface detail imparted by this manufacturing method also provides the lens with a surface finish which meets optical standards without subsequent polishing. By normalizing and contouring the lens or lens blank prior to hot stamping, residual stresses are minimized. Material displacements and resulting stress imparted by hot stamping are kept to a minimum. The manufacturing method causes no significant detrimental chemical or physical changes in the polymer material. The method can be utilized for most lens configurations without undercuts, including multifocal and monovision surfaces, aspheric, toric, or peripheral radii, and non-concentric peripheries in either the same or dissimilar planes. Undercut surfaces can also be hot stamped using subsequent hot stamping steps and different dies.

Although the present invention has been described with reference to preferred embodiments, those skilled in the art will recognize that changes may be made in form and detail without departing from the spirit and scope of the invention.

What is claimed is:

1. A method for manufacturing an intraocular lens body from a sheet of polymer characterized by a glass transition temperature and a melt flow temperature, including:
   machining, from the sheet of polymer, a lens member having a lens generation area with a surface and contoured to correspond to the desired contour of the finished lens, the lens member machined to a predetermined precompensated size larger than desired to accommodate normalizing shrinkage;
   normalizing the lens member and causing the lens member to shrink to the desired size;
   providing a stamping die having an optical embossing surface contoured as a physical negative of the lens generation area and bearing a physical negative of desired optical surface structure of the lens;
   forcing the optical embossing surface of the stamping die and the surface of the lens member into engagement with one another at a predetermined stamping pressure and for a predetermined stamping dwell time period;
   applying sufficient energy to heat the surface of the lens member to a temperature between the glass transition temperature and the melt flow temperature of the polymer member and emboss the optical surface structure onto the surface of the lens generation area; and
   removing the optical embossing surface of the stamping die from the polymer lens member following the expiration of the stamping dwell time period.

2. The method of claim 1 wherein applying energy includes heating the stamping die.

3. The method of claim 1 and further including cooling the stamping die and lens member during the dwell time period.

4. The method of claim 1 and further including preheating the lens member before forcing the die and lens member into engagement with one another.

5. The method of claim 1 wherein applying energy includes applying ultrasonic energy for at least a portion of the dwell time period.

6. The method of claim 1 wherein forcing the embossing surface and the lens member into engagement with one another includes fixedly positioning the lens member and forcing the embossing surface into engagement with the surface of the lens member.

7. The method of claim 1 wherein machining the lens member includes machining the lens member from a polymethylmethacrylate sheet.

8. The method of claim 1 wherein normalizing the lens member includes heating the lens member in a vacuum oven.

9. The method of claim 8 and further including releasing the vacuum from the oven by introducing dry nitrogen.

10. The method of claim 9 and storing the normalized lens member in a container having a low vapor transmission rate.

11. The method of claim 1 and further including forcing the embossing surface and the surface of the lens member into engagement in an anaerobic environment.

12. The method of claim 1 wherein providing a stamping die includes providing a stamping die having an embossing surface configured to first contact a center of the surface of the lens member and having an area of contact with the surface which progressively extends radially outwardly to facilitate gas venting as the embossing surface is forced into engagement with the surface of the lens member.

13. The method of claim 1 wherein providing the polymer lens member includes providing a lens member having a gas vent groove extending across at least a portion of the surface of the lens generation area.

14. The method of claim 1 wherein:
   providing a stamping die includes providing a stamping die having an embossing surface configured to first contact a center of the surface of the lens member and having an area of contact with the surface which progressively extends radially outwardly to facilitate gas venting as the embossing surface is forced into engagement with the surface of the lens member; and
   providing the polymer lens member includes providing a lens member having a gas vent groove extending across at least a portion of the surface.

15. The method of claim 1 wherein providing the stamping die includes providing a stamping die having an embossing surface bearing a physical negative of a complex optical surface structure.

16. The method of claim 15 wherein providing the stamping die includes providing a stamping die having an embossing surface bearing a physical negative of a multicurved optical surface.

17. The method of claim 15 wherein providing the stamping die includes providing a stamping die having an embossing surface bearing a physical negative of an aspheric optical surface.

18. The method of claim 15 wherein providing the stamping die includes providing a stamping die having an embossing surface bearing a physical negative of a diffractive multifocal optical surface.

19. The method of claim 15 wherein providing the stamping die includes providing a stamping die having an embossing surface bearing a physical negative of a refractive multifocal optical surface.

20. The method of claim 15 wherein providing the stamping die includes providing a stamping die having an embossing surface bearing a physical negative of a toric optical surface.

21. The method of claim 1 wherein providing the stamping die includes providing a stamping die having an embossing surface bearing a physical negative of a single curve optical surface.

22. The method of claim 1 wherein:
fabricating the lens member includes fabricating a one-piece polymer lens blank including the contoured lens generation area and a contoured haptic generation area with a surface about the periphery of the lens generation area;
providing the stamping die includes providing a stamping die having a contoured optical embossing surface and a peripheral haptic embossing surface contoured as a physical negative of the haptic generation area and bearing a physical negative of desired haptic structure of the lens;
forcing the embossing surface includes forcing the optical embossing surface and haptic embossing surface of the stamping die and the respective lens generation and haptic generation area surfaces of the lens blank into engagement with one another at a predetermined stamping pressure and for a predetermined stamping dwell time period;
applying sufficient energy includes applying sufficient energy to heat the surfaces of the lens member to temperatures between the glass transition temperature and the melt flow temperature of the polymer member and emboss the optical surface structure and haptic structure onto the surfaces of the lens blank; and
removing the embossing surface includes removing the optical embossing surface and the haptic embossing surface from the lens blank following the expiration of the stamping dwell time period.

23. A method for manufacturing an intraocular lens body from a cell cast sheet of high molecular weight polymethylmethacrylate characterized by a glass transition temperature and a melt flow temperature, including:
machining from the sheet of polymethylmethacrylate a lens blank having a lens generation area with a surface and contoured to correspond to the desired contour of the finished lens, the lens blank machined to a predetermined precompensated size larger than desired to accommodate normalizing shrinkage;
normalizing the lens blank by heating the lens blank in a vacuum oven;
releasing the vacuum from the oven by introducing dry gas;
providing a stamping die having an optical embossing surface contoured as a physical negative of the lens generation area and bearing a physical negative of desired optical surface structure of the lens;
forcing the embossing surface of the stamping die into engagement with the lens generation area of the blank at a predetermined stamping pressure and for a predetermined stamping dwell time;
applying sufficient energy to the lens generation area of the lens blank to heat the lens generation area to a temperature between the glass transition temperature and the melt temperature and emboss the optical surface structure onto the surface of the lens generation area; and
removing the optical embossing surface of the stamping die from the lens blank following the expiration of the stamping dwell time.

24. The method of claim 23 wherein applying sufficient energy includes heating the stamping die.

25. The method of claim 23 wherein applying sufficient energy includes applying ultrasonic energy to the engaged stamping die and lens blank.

26. The method of claim 23 wherein providing a stamping die includes providing a stamping die having an embossing surface configured to first contact a central portion of the lens generation area and having an area of contact with the lens generation area which extends progressively radially outwardly as the embossing surface and lens generation area are engaged.

27. The method of claim 23 wherein providing the lens blank includes providing a lens blank having a gas vent groove extending across at least a portion of the lens generation area.

28. The method of claim 23 wherein:
providing a stamping die includes providing a stamping die having an embossing surface configured to first contact a center of the surface of the lens member and having an area of contact with the surface which progressively extends radially outwardly to facilitate gas venting as the zone plate reproducing surface is forced into engagement with the surface of the lens member; and
providing the polymer lens member includes providing a lens member having a gas vent groove extending across at least a portion of the surface.

29. The method of claim 23 wherein:
machining a lens blank includes machining a one piece blank including a contoured lens generation area and a contoured haptic generation area with a surface about the periphery of the lens generation area;
providing the stamping die includes providing a stamping die having a contoured optical embossing surface and a peripheral haptic embossing surface contoured as a physical negative of the haptic generation area and bearing a physical negative of desired haptic structure of the lens;
forcing the embossing surface includes forcing the optical embossing surface and haptic embossing surface of the stamping die and the respective lens generation and haptic generation area surfaces of the lens blank into engagement with one another;
applying sufficient energy includes applying sufficient energy to emboss the optical surface structure and haptic structure onto the surfaces of the lens blank; and
removing the embossing surface includes removing the optical embossing surface and the haptic embossing surface from the lens blank.

30. The method of claim 23 wherein providing the stamping die includes providing a stamping die having an embossing surface bearing a physical negative of a single curve optical surface.

31. The method of claim 23 wherein providing the stamping die includes providing a stamping die having an embossing surface bearing a physical negative of a complex 32. The method of claim 31 wherein providing the stamping die includes providing a stamping die having an embossing surface bearing a physical negative of a multicurved optical surface.

33. The method of claim 31 wherein providing the stamping die includes providing a stamping die having an embossing surface bearing a physical negative of a toric optical surface.

34. The method of claim 31 wherein providing the stamping die includes providing a stamping die having an embossing surface bearing a physical negative of an aspheric optical surface.

35. The method of claim 31 wherein providing the stamping die includes providing a stamping die having an embossing surface bearing a physical negative of a diffractive multifocal optical surface.

36. The method of claim 31 wherein providing the stamping die includes providing a stamping die having an embossing surface bearing a physical negative of a refractive multifocal optical surface.

37. A method for manufacturing an intraocular lens body, including:
fabricating a polymer lens member having a lens generation area with a surface and contoured to correspond to the desired contour of the finished lens, the polymer characterized by a glass transition temperature and a melt flow temperature;
providing a stamping die having an optical embossing surface contoured as a physical negative of the lens generation area and bearing a physical negative of a desired complex optical surface structure of the lens, the complex surface structure selected from the set including a multicurved optical surface, a multicurved aspheric optical surface, a diffractive multifocal optical surface, a refractive multifocal optical surface, and a toric optical surface;
forcing the optical embossing surface of the stamping die and the surface of the lens member into engagement with one another at a predetermined stamping pressure and for a predetermined stamping dwell time period;
applying sufficient energy to heat the surface of the lens member and emboss the complex optical surface structure onto the surface of the lens generation area; and
removing the optical embossing surface of the stamping die from the polymer lens member following the expiration of the stamping dwell time period.

38. The method of claim 37 wherein applying energy includes heating the stamping die.

39. The method of claim 37 and further including cooling the stamping die and lens member during the dwell time period.

40. The method of claim 37 and further including preheating the lens member before forcing the die and lens member into engagement with one another.

41. The method of claim 37 wherein applying energy includes applying ultrasonic energy for at least a portion of the dwell time period.

42. The method of claim 37 wherein fabricating the lens member includes fabricating the lens member from polymethylmethacrylate.

43. The method of claim 37 wherein providing the polymer lens member includes providing a lens member having a gas vent groove extending across at least a portion of the surface of the lens generation area.

44. The method of claim 38 wherein:
providing a stamping die includes providing a stamping die having an embossing surface configured to first contact a center of the surface of the lens member and having an area of contact with the surface which progressively extends radially outwardly to facilitate gas venting as the embossing surface is forced into engagement with the surface of the lens member; and
providing the polymer lens member includes providing a lens member having a gas vent groove extending across at least a portion of the surface.

45. The method of claim 37 wherein:
fabricating the lens member includes fabricating a one-piece polymer lens blank including the contoured lens generation area and a contoured haptic generation area with a surface about the periphery of the lens generation area;
providing the stamping die includes providing a stamping die having a contoured optical embossing surface and a peripheral haptic embossing surface contoured as a physical negative of the haptic generation area and bearing a physical negative of desired haptic structure of the lens;
forcing the embossing surface includes forcing the optical embossing surface and haptic embossing surface of the stamping die and the respective lens generation and haptic generation area surfaces of the lens blank into engagement with one another at a predetermined stamping pressure and for a predetermined stamping dwell time period;
applying sufficient energy includes applying sufficient energy to heat the surfaces of the lens member to emboss the optical surface structure and haptic structure onto the surfaces of the lens blank; and
removing the embossing surface includes removing the optical embossing surface and the haptic embossing surface from the lens blank following the expiration of the stamping dwell time period.

46. The method of claim 37 wherein fabricating the lens member includes fabricating the lens member from Perspex PMMA.

47. The method of claim 37 wherein applying energy includes applying sufficient energy to heat the surface of the lens member to a temperature between the glass transition temperature and the melt flow temperature of the member.

* * * * *